(12) United States Patent
Meethal et al.

(10) Patent No.: US 7,546,770 B2
(45) Date of Patent: Jun. 16, 2009

(54) ELECTROMAGNETIC ACOUSTIC TRANSDUCER

(75) Inventors: Manoj Kumar Koyithitta Meethal, Kerala (IN); David Martin Paige, Tyne and Wear (GB)

(73) Assignee: General Electric Company, Niskayuna, NY (US)

( * ) Notice: Subject to any disclaimer, the term of this patent is extended or adjusted under 35 U.S.C. 154(b) by 375 days.

(21) Appl. No.: 11/325,945

(22) Filed: Jan. 5, 2006

(65) Prior Publication Data

US 2007/0151344 A1    Jul. 5, 2007

(51) Int. Cl.
G01N 29/24 (2006.01)
(52) U.S. Cl. ........................................ 73/643
(58) Field of Classification Search ............. 73/643
See application file for complete search history.

(56) References Cited

U.S. PATENT DOCUMENTS

| 4,149,421 | A | * | 4/1979 | Buttcher et al. ............. 73/643 |
| 4,665,752 | A | * | 5/1987 | Huschelrath et al. .......... 73/643 |
| 4,777,824 | A | | 10/1988 | Alers et al. ................ 73/643 |
| 5,050,703 | A | * | 9/1991 | Graff et al. ................ 181/106 |
| 5,168,760 | A | * | 12/1992 | Wun-Fogle et al. ........... 73/779 |
| 5,537,876 | A | * | 7/1996 | Davidson et al. ............. 73/624 |
| 5,608,691 | A | * | 3/1997 | MacLauchlan et al. ....... 367/140 |
| 5,684,406 | A | * | 11/1997 | MacLauchlan et al. ....... 324/700 |
| 5,721,379 | A | | 2/1998 | Palmer et al. ............... 75/643 |
| 6,070,467 | A | * | 6/2000 | Rosenberg et al. ........... 73/643 |
| 6,109,108 | A | * | 8/2000 | Ohtani et al. ............... 73/599 |
| 6,766,694 | B2 | * | 7/2004 | Hubschen ................. 73/643 |

FOREIGN PATENT DOCUMENTS

| DE | 3904440 A1 | * | 8/1990 |
| GB | 2385229 A | * | 8/2003 |
| GB | 2403011 A | | 12/2004 |
| GB | 2403011 A | * | 12/2004 |
| WO | WO 2004/113906 A1 | * | 12/2004 |

* cited by examiner

*Primary Examiner*—Daniel S Larkin
*Assistant Examiner*—Rose M Miller
(74) *Attorney, Agent, or Firm*—Patrick K. Patnode

(57) ABSTRACT

An electromagnetic acoustic transducer (EMAT) for inspecting an object is provided. The EMAT includes a magnet configured to generate a magnetic field in an object and a radio frequency coil configured to induce eddy currents on a surface of the object. The EMAT further includes a laminated wear plate disposed over the magnet and the radio frequency coil and configured to shield the magnet and the radio frequency coil from damage.

20 Claims, 7 Drawing Sheets

ELECTROMAGNETIC ACOUSTIC TRANSDUCER

BACKGROUND

The invention relates generally to inspection systems and more specifically to electromagnetic acoustic transducers for use in ultrasonic inspection systems.

Ultrasonic inspection is a commonly used non-destructive evaluation (NDE) technique for detecting corrosion and cracking in different objects such as metallic components, pipes, and so forth. Electromagnetic acoustic transducers (EMATs) are ultrasonic transducers that couple acoustic energy into and out of an object electromagnetically rather than through the use of an acoustic coupling medium such as water.

The absence of a coupling medium enables electromagnetic acoustic transducers to be used in a variety of applications where the use of the coupling medium between the transducer and the specimen is either impractical or undesirable. For example, if the specimen is coated with an acoustically attenuating material, acoustic wave propagation is not feasible. The absence of the coupling medium also improves reliability of the scanning process and hence reduces the risk of having to perform repeated inspections in cases where the coupling medium has been lost. The use of EMATs enables inspection at elevated temperatures, on moving objects, in vacuum, on oily or rough surfaces and also in remote locations.

An EMAT generates ultrasonic energy in an object by applying a magnetic field to the object using a magnet, and inducing radio frequency (RF) eddy-currents into the object using an RF coil. The RF pulses interact with the magnetic field to produce a Lorentz force, which in turn produces ultrasonic waves at the radio frequency in the object. The strength of the generated force depends on the proximity of the probe to the object.

A wear plate is commonly attached to the electromagnetic acoustic transducer to protect the magnets and the RF coil from wear due to the motion of EMAT and contact with other components, such as the objects being inspected. Typically, the wear plate is made of protective material layers. Such materials are usually electrically non conductive and non-ferromagnetic. For example, certain EMATs use a ceramic wear plate. The wear plate is usually disposed between an inspecting region on the object and the EMAT. Since the wear plates are made using materials that are neither electrically conductive nor ferromagnetic, the wear plates introduce higher reluctance paths between the active part of the EMAT and the inspected region. Such reluctance paths cause flux leakage between the poles of the magnet, which in turn reduces the strength of the magnetic field in the object.

One way to minimize the reluctance path is by using wear plates having relatively thin protective layers. One disadvantage with using thin layer wear plates is that the lifetime of the EMAT is significantly reduced. Increasing the thickness of the protective layer of the wear plate on the other hand, results in a decline of the force generated by the EMAT. Additional lift-off from the surface causes the force generation to be much weaker and hence degrades the inspection signals.

Thus, there is a need for a wear plate for an electromagnetic transducer that can retain the electromagnetic force while minimizing flux leakage.

BRIEF DESCRIPTION

Briefly, in accordance with one aspect of the invention, an electromagnetic acoustic transducer (EMAT) for inspecting an object is provided. The EMAT includes a magnet configured to generate a magnetic field in an object and a radio frequency coil configured to induce eddy currents on a surface of the object. The EMAT further includes a laminated wear plate disposed over the magnet and the radio frequency coil and configured to shield the magnet and the radio frequency coil from damage. In a further specific embodiment, the laminated wear plate comprises a plurality of ferromagnetic layers and an electrically conductive coating coated on an outer surface of the laminated wear plate.

In an alternate embodiment, an ultrasonic inspection system for inspecting an object is provided. The system comprises an electromagnetic acoustic transducer (EMAT) including a laminated wear plate and an ultrasound receiver. The ultrasound receiver is coupled to the EMAT and configured to convert acoustic signals received from the object to corresponding electrical signals.

In another embodiment, an ultrasonic method for inspecting an object is provided. The method comprises aligning lines of magnetic flux in a direction generally perpendicular to the object using a laminated wear plate coupled to an electromagnetic acoustic transducer. The method further includes inducing eddy currents in a direction generally parallel to the object and processing acoustic signals received from the object to generate information representative of a condition of the object.

In another embodiment, a kit for shielding an electromagnetic assembly is provided. The kit comprises a laminated wear plate comprising a plurality of ferromagnetic layers. The laminated wear plate is coated with an electrically conductive material.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The described embodiments are generally directed towards an EMAT, which may be used for non-destructive inspection applications. Such applications may include, without limitation, pipe inspection systems, pressure vessel inspection, and so forth, and generally provide useful two-dimensional and three-dimensional data and context. To facilitate explanation, however, pipe inspection implementations will be generally discussed herein, though it is to be understood that other inspection implementations are also within the scope of the present invention.

Figure 1:
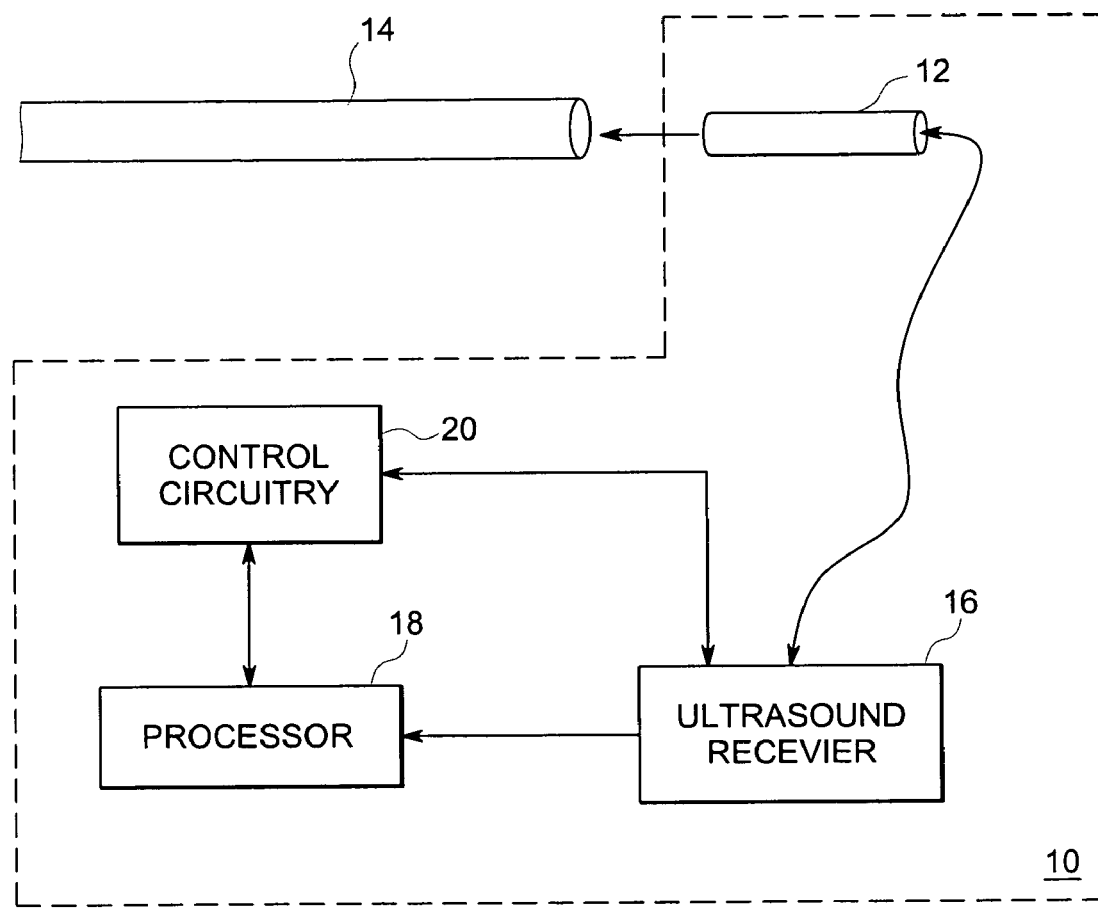
FIG. 1 is a diagrammatic representation of an ultrasonic inspection system using an EMAT, in accordance with an exemplary embodiment.

Turning now to the drawings, and referring first to FIG. 1, ultrasonic inspection system 10 implements an EMAT in conjunction with an ultrasound receiver system to inspect an object. For the purpose of this description, the object comprises pipe 14. Each block is explained in further detail below.

EMAT 12 is configured to generate ultrasonic waves directly in the electrically conductive material via electromagnetic fields. The EMAT is further configured to receive acoustic signals representative of an area being inspected on pipe 14. The EMAT is attached to a laminated wear plate configured to shield electromagnetic components in the transducer from wear due to motion or contact with elements, such as the pipe or other surrounding components. The structure and operation of the EMAT itself will be described in further detail with reference to FIG. 2 and FIG. 3.

Continuing with FIG. 1, the ultrasonic inspection system further comprises an ultrasound receiver 16 coupled to the EMAT 12. The receiver is configured to receive the acoustic signals that are representative of the area of the object being inspected. The receiver system converts acoustic signals to electrical signals for further processing by processor 18. The ultrasound receiver is further configured to excite electromagnetic components in the EMAT 12 by supplying radio frequency pulses. Exemplary pulses include spike pulses and square wave pulses. The frequency of the pulses may be set via control circuitry 20.

Processor 18 receives the electrical signals generated by ultrasound receiver system 16. Control circuitry 20 is further configured to provide control signals indicative of the waveform characteristics (i.e., frequency, amplitude, and so forth) of the applied pulses to processor 18. The processor may apply various signal processing algorithms on the received data to generate required information, such as data indicative of the presence of flaws, cracks, and so forth in the pipe being inspected.

Figure 2:
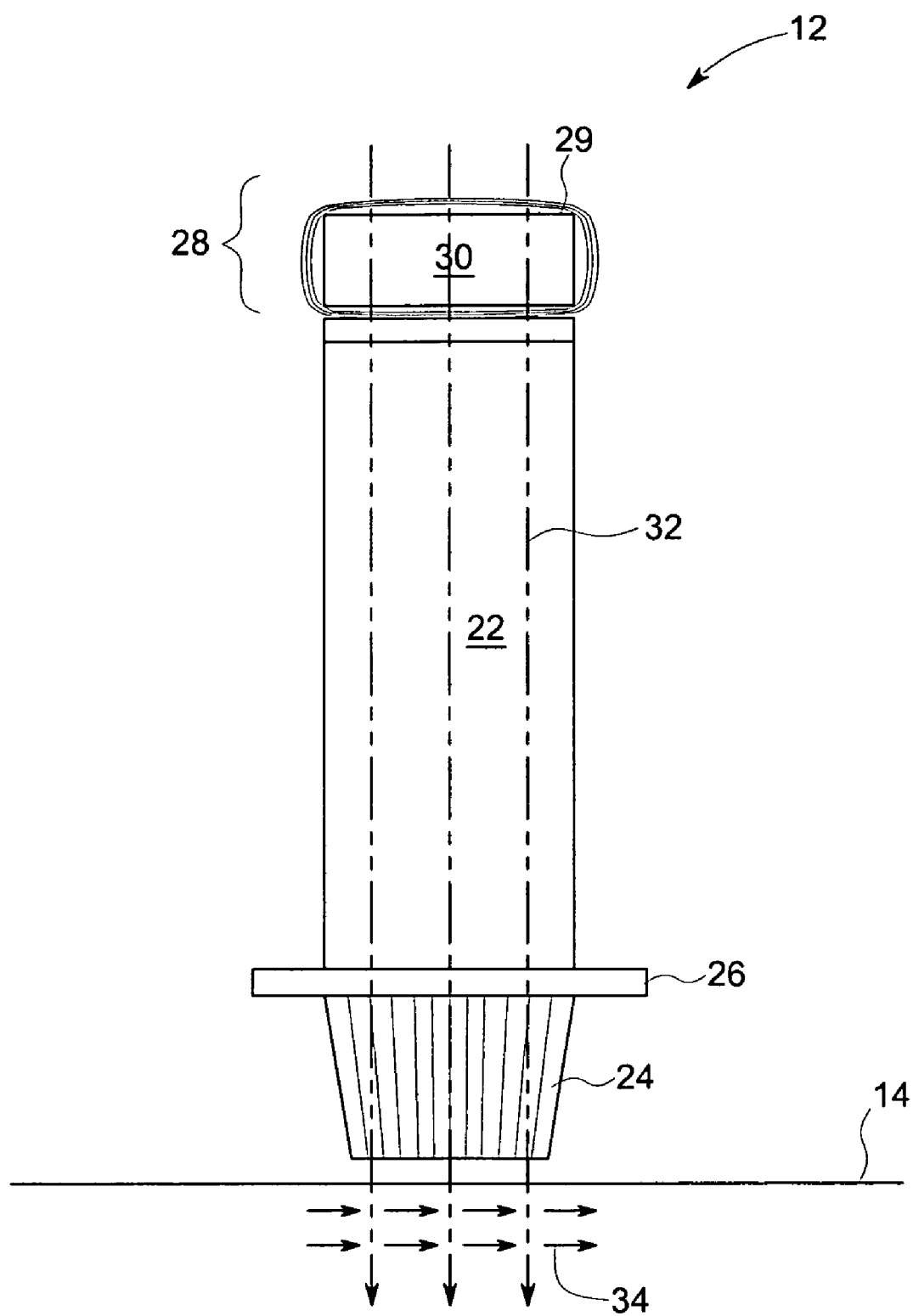
FIG. 2 is a cross section of an EMAT, in accordance with an exemplary embodiment.

FIG. 2 is a cross section of one embodiment of an EMAT. To facilitate explanation, a shear wave EMAT will be generally discussed herein, though it is to be understood that other EMATs such as Rayleigh EMATs are alternative embodiments. The EMAT comprises a magnet 22, a radio frequency coil 28 and a laminated wear plate 24. Each component is described in further detail below.

Magnet 22 is configured for generating or inducing a magnetic field in the object. As is well known to those skilled in the art, the magnetic field is required for efficient generation of ultrasound via the Lorentz force or magnetostriction mechanisms. In particular embodiments, magnet 22 may comprise a permanent magnet or periodic permanent magnets.

Radio frequency (RF) coil 28 is configured to generate a time-varying magnetic field based on the current flowing in the coil. The time-varying field induces eddy currents around the area being inspected by the EMAT. The RF coil comprises an iron core 30 wound with a conductor 29. The eddy currents induced by the radio frequency coil 28 and the magnetic field generated by the magnet 22 cause Lorentz forces in the object.

Laminated wear plate 24 is attached to magnet 22 via an insulation layer 26. The laminated wear plate comprises several ferromagnetic layers stacked together. The ferromagnetic layers create a low reluctance path between the EMAT and the pipe. The laminated wear plate is configured to channel the magnetic field and eddy currents in a desired direction. Specifically, the laminated wear plate is configured to align lines of magnetic flux 32 emanating form the transducer in a direction generally perpendicular to the object.

The low reluctance path is created between the magnet and the pipe improves the flux linkage between the pipe and the EMAT. The laminated wear plate is further coated with a highly conductive material to enable a strong eddy current flow on an inspecting surface of the pipe 14. The conductive coating aligns the induced eddy currents 34 in a direction generally parallel to the object.

Figure 3:
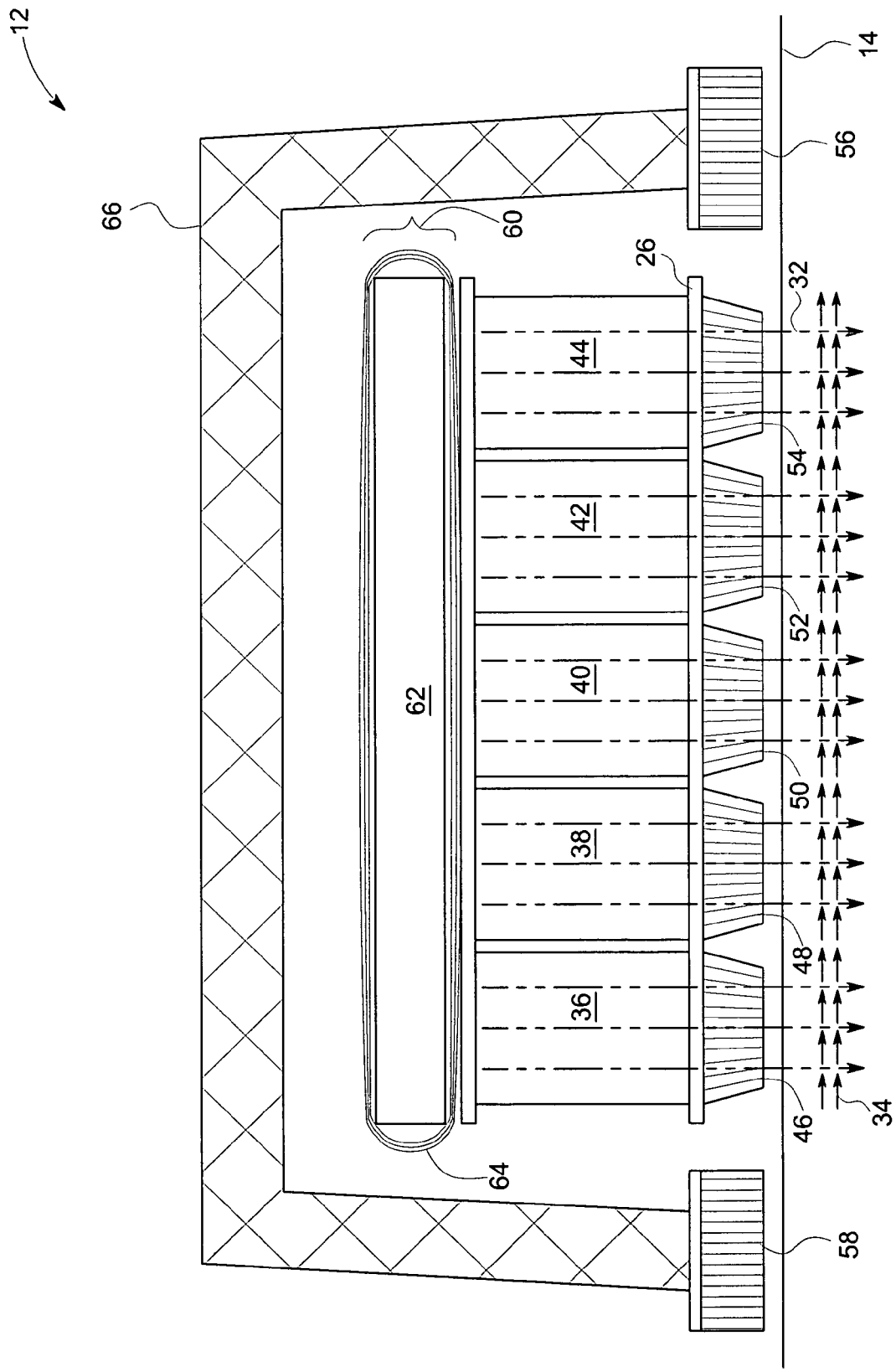
FIG. 3 is a cross section of an alternate embodiment of an EMAT.

FIG. 3 is a cross sectional view of another embodiment of an EMAT with laminated wear plates arranged in slots. The EMAT 12 comprises magnets 36, 38, 40, 42 and 44, and a radio frequency coil 60. The magnets and the radio frequency coil are enclosed in housing structure 66. Radio frequency coil 60 is disposed over the magnets. The radio frequency coil comprises iron core 62 with conductive windings 64 wound around the core. As described with reference to FIG. 2, the EMAT operates on the principle of Lorentz force created by the magnetic field and the induced eddy currents.

In the illustrated embodiment, each magnet is attached to a corresponding laminated wear plate 46, 48, 50, 52 and 54 respectively thus forming a slotted arrangement. Laminated wear plates 56 and 58 are also attached to housing 68. The laminated wear plates are configured to align the flux lines 32 in a direction generally perpendicular to the object, and to align the eddy currents 34 in a direction generally parallel to the object.

The slotted arrangement reduces flux leakage between adjacent magnets, such as between magnets 36 and 38. The arrangement also reduces flux concentration at the corners of each magnet, which minimizes leakage within slots at higher lift-off. Lift-off is defined as a maximum distance at which the EMAT can be positioned from the inspecting surface of the object without causing a significant decay in the electromagnetic field for a particular input power. Typically, lift-off is proportionate to the input power applied to the EMAT. The laminated wear plate aids in increasing the lift-off for a specific operating frequency and input power. In one embodiment, the lift-off is 2 mm for an EMAT operating at 270 KHz frequency. The structure of the laminated wear plate is described in further detail below.

Figure 4:
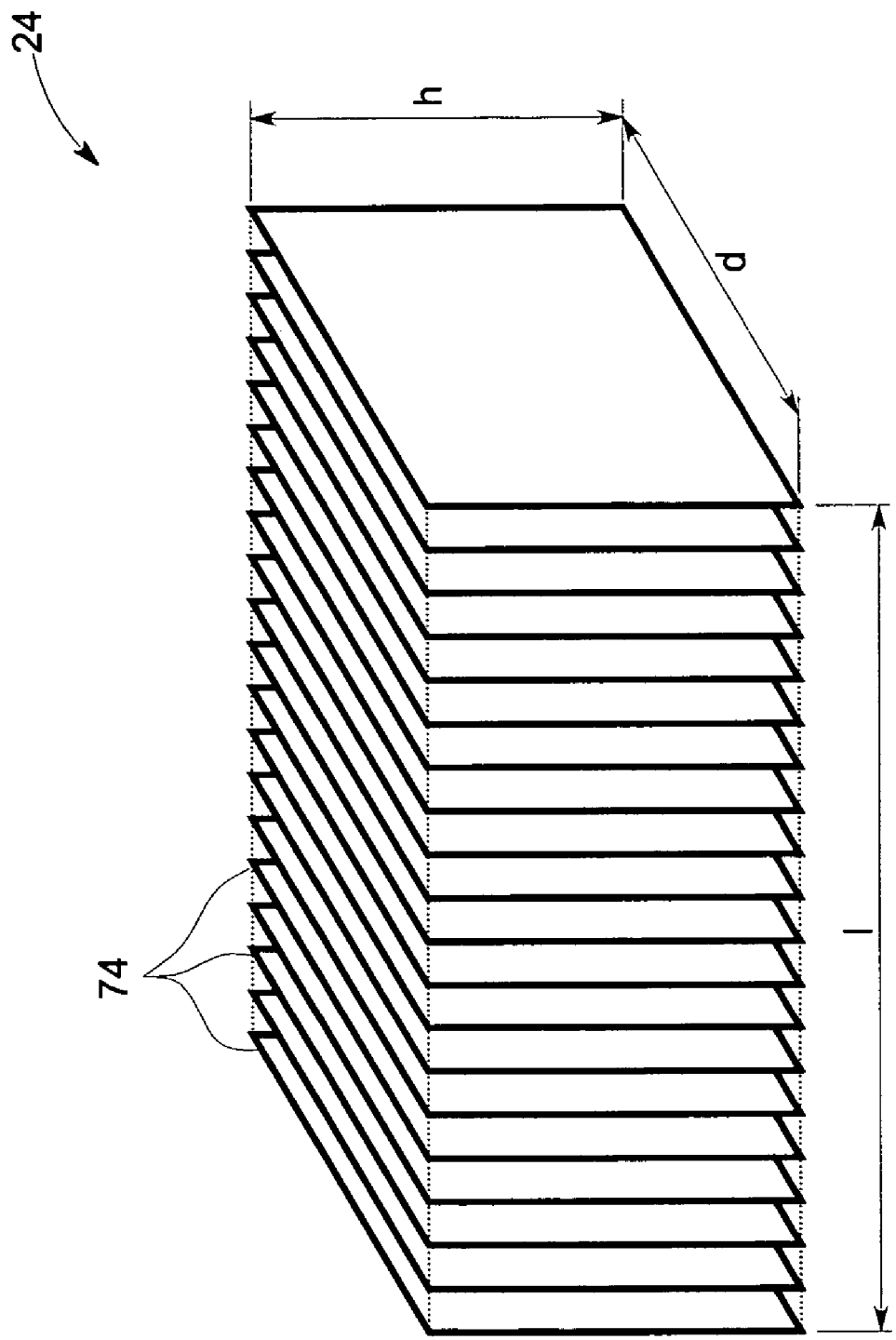
FIG. 4 is a perspective view of a laminated wear plate in accordance with an exemplary embodiment.

FIG. 4 is a perspective view of a laminated wear plate implemented in the EMATs described in FIG. 2 and FIG. 3. The laminated wear plate includes a plurality of ferromagnetic layers 74. A thin layer of epoxy (not shown) is present between the ferromagnetic layers. In a specific embodiment, a length of the laminated wear plate 'l' is 2 millimeters (mm), a height 'h' of the laminated wear plate is 2 mm and a depth 'd' of the laminated wear plate is 28 mm.

Figure 5:
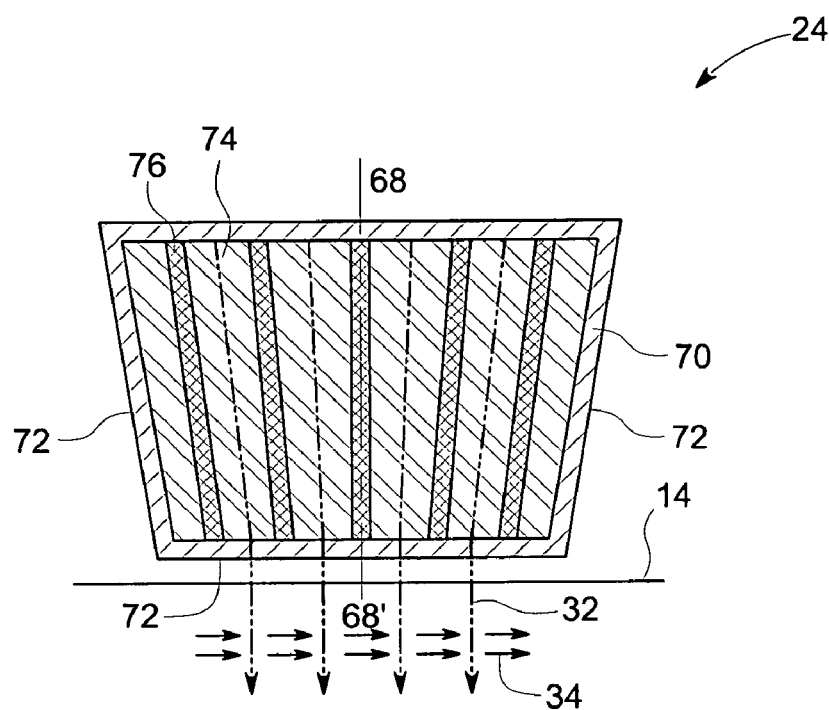
FIG. 5 is a cross-sectional view of a laminated wear plate in accordance with an exemplary embodiment.

FIG. 5 is a cross sectional view of an exemplary laminated wear plate used for the EMATs described above. The laminated wear plate 24 comprises a plurality of ferromagnetic layers 74. In one embodiment, a thickness 'T' of ferromagnetic layer is 0.018 mm. Thin layers 76 of epoxy may be disposed between the ferromagnetic layers. In one embodiment, a thickness 't' of the thin layer is 0.002 mm. The laminated wear plate aligns the flux lines 32 in a direction generally perpendicular to the object 14.

The laminated wear plate 24 is coated with an electrically conductive material 70 on its outer surfaces 72. In one embodiment, the electrically conductive material is copper. The coating of electrically conductive material aids in aligning the induced eddy currents 34 in a direction generally parallel to the object.

Figure 6:
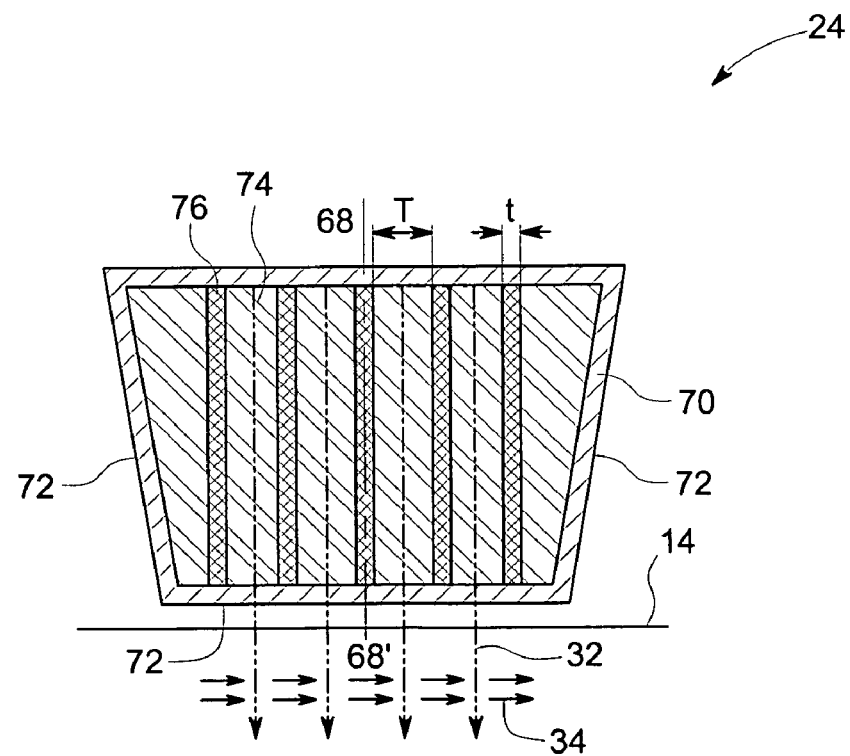
FIG. 6 is a cross-sectional view of an alternate embodiment of a laminated wear plate.

In the illustrated embodiment, the ferromagnetic layers are disposed at an angle with respect to the vertical axis 68-68' of the laminated wear plate. In another embodiment, illustrated in FIG. 6, the ferromagnetic layers 74 are disposed in parallel to the vertical axis 68-68' of the laminated wear plate. In an alternate embodiment, the ferromagnetic layers are disposed in a grid like pattern.

Figure 7:
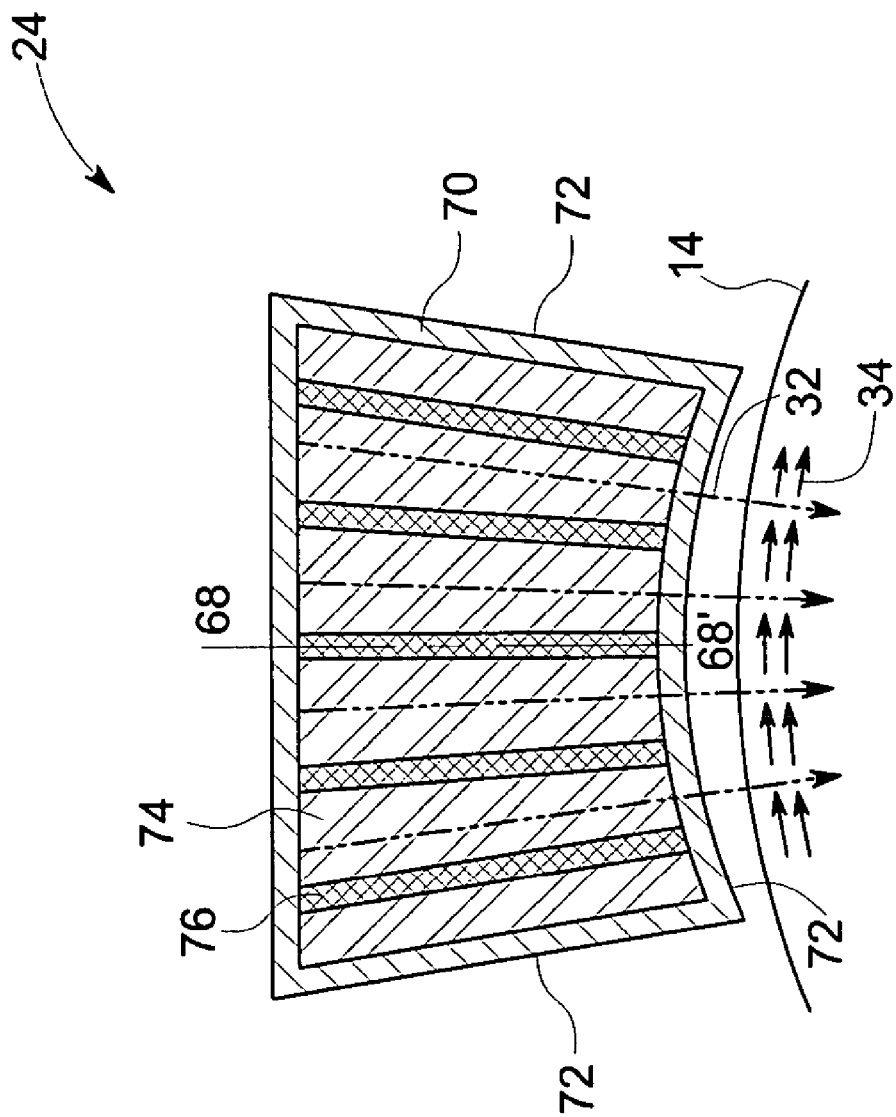
FIG. 7 is a cross-section view of another embodiment of a laminated wear plate.

For inspecting curved areas, the laminated wear plate can be configured to align flux lines 32 generally perpendicular to a tangent of the curvature of the inspected area, as shown in FIG. 7. The eddy currents 32 would then be aligned generally in parallel to the tangent of the curved surface.

Figure 8:
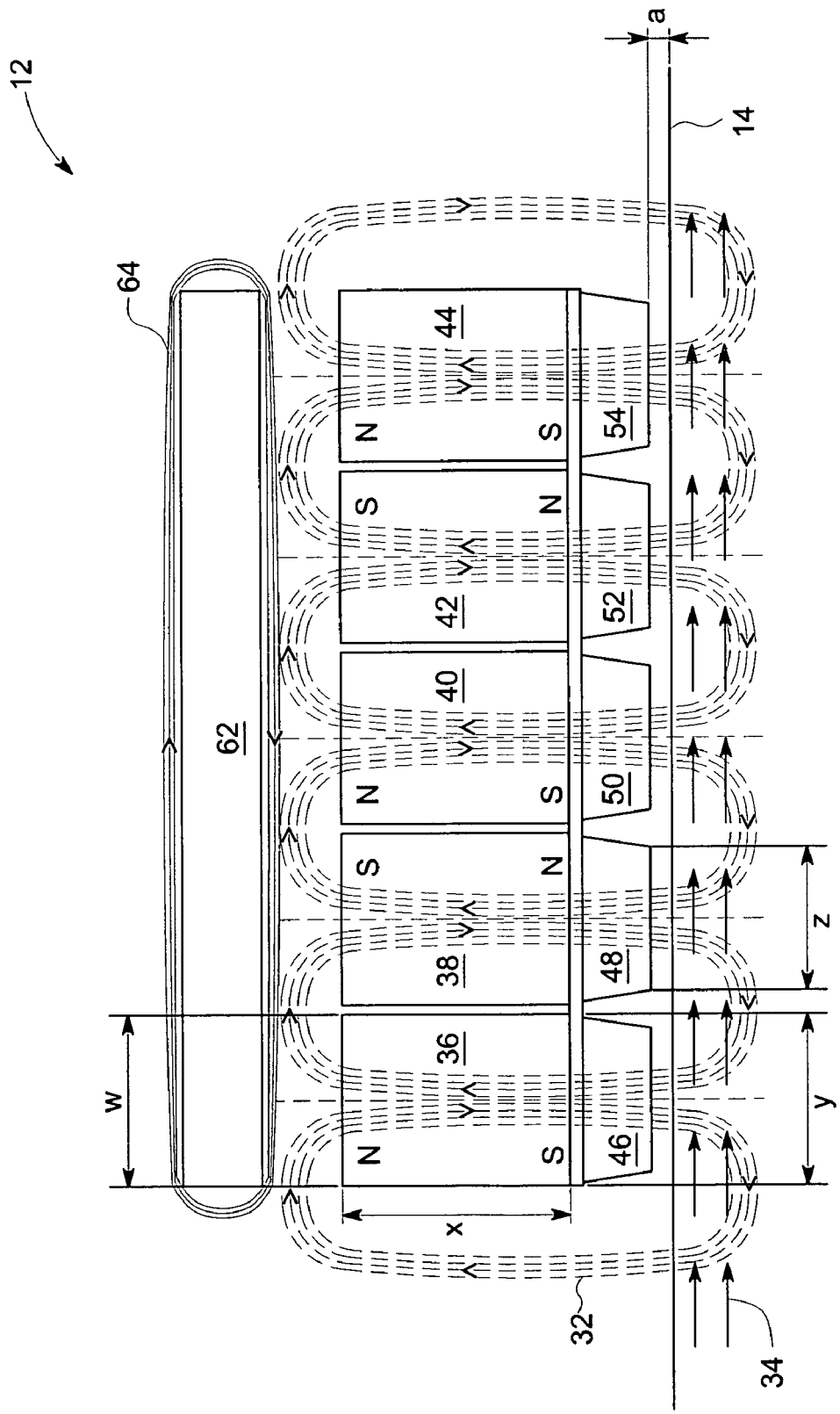
FIG. 8 is a cross-sectional view of an embodiment of an EMAT in accordance with an exemplary embodiment.

FIG. 8 is a cross-section of an EMAT. In the illustrated embodiment, magnets 36, 38, 40, 42 and 44 are of 'w' width and 'x' height. In one embodiment, 'w' is 3.5 mm and 'x' is 5 mm. The thickness of the magnets is 28 mm. The laminated wear plates have an outer width and an inner width. The outer width represented by 'y', is the width of the side of the laminated wear plate that is attached to the magnet. The inner width represented by 'z', is the width of the side of the laminated wear plate that is closer to the object 14. In one embodiment, the outer width of the laminated wear plate is 3 mm and the inner dimension is 2 mm. The distance (lift-off) between the inner width of the laminated plate and an inspecting surface of the object 14 is represented by 'a'. In the illustrated embodiment, 'a' is 0.05 mm.

The above described laminated wear plate has many advantages over conventional ceramic wear plates, including increased life and low power consumption. Moreover, the laminated wear plate of the present invention enables the EMAT to be operable at higher lift-off as it provides improved flux linkage. Furthermore, the conductive coating on the laminated wear plate restricts the eddy currents to the outer surface of the laminated wear plate thus reducing power consumption for a given operating frequency and input power.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An electromagnetic acoustic transducer (EMAT) for inspecting an object, comprising:
   a magnet configured to generate a magnetic field in an object;
   a radio frequency coil configured to induce eddy currents on a surface of the object; and
   a laminated wear plate disposed over the magnet and the radio frequency coil and configured to shield the magnet and the radio frequency coil from damage, wherein the laminated wear plate comprises a plurality of ferromagnetic layers.

2. The EMAT of claim 1, wherein the laminated wear plate is coated with an electrically conductive material.

3. The EMAT of claim 2, wherein the electrically conductive material is coated on an outer surface of the laminated wear plate.

4. The EMAT of claim 3, wherein the electrically conductive material is copper.

5. The EMAT of claim 1, wherein the laminated wear plate is configured to align lines of magnetic flux emanating form the transducer in a direction generally perpendicular to the object.

6. The EMAT of claim 1, wherein the laminated wear plate is configured to align eddy currents in a direction generally parallel to the object.

7. An electromagnetic acoustic transducer (EMAT) for inspecting an object comprising:
   a magnet configured to generate a magnetic field;
   a radio frequency coil configured to induce eddy currents on a surface of the object;
   a laminated wear plate disposed over the magnet and the radio frequency coil and configured to shield the magnet and the RF coil from damage, the laminated wear plate comprising:
      a plurality of ferromagnetic layers,
      an electrically conductive coating coated on an outer surface of the laminated wear plate.

8. The EMAT of claim 7, wherein the plurality of ferromagnetic layers are stacked at an angle with respect to a vertical axis of the laminated wear plate.

9. The EMAT of claim 7, wherein the plurality of ferromagnetic layers are parallel to a vertical axis of the laminated wear plate.

10. The EMAT of claim 7, wherein the EMAT comprises a shear EMAT.

11. The EMAT of claim 7, wherein the EMAT comprises a Rayleigh EMAT.

12. An ultrasonic inspection system for inspecting an object; the system comprising:
   an electromagnetic acoustic transducer (EMAT) comprising:
      a magnet configured to generate a static magnetic field;
      a radio frequency coil configured to induce eddy currents on a surface of the object;
      a laminated wear plate coupled to the magnet and configured to shield the magnet and the RF coil from damage comprising:
         a plurality of ferromagnetic layers; and
         an electrically conductive coating coated on an outer surface of the laminated wear plate; and
   an ultrasound receiver system coupled to the EMAT and configured to convert acoustic signals received from the object to corresponding electrical signals.

13. The system of claim 12, wherein the EMAT further comprises an insulating layer disposed above a top surface of the laminated wear plate.

14. The system of claim 12, further comprising control circuitry to provide control signals to the ultrasound receiver and the processor.

15. A ultrasonic method for inspecting an object, the method comprising
   aligning lines of magnetic flux in a direction generally perpendicular to the object; wherein the aligning is achieved using a laminated wear plate coupled to an electromagnetic acoustic transducer;
   inducing eddy currents in a direction generally parallel to the object; and
   processing acoustic signals received from the object to generate information representative of a condition of the object.

16. The method of claim 15, wherein the laminated wear plate comprises a plurality of ferromagnetic layers.

17. The method of claim 15, further comprising coating the laminated plate with an electrically conductive material.

18. A kit for shielding an electromagnetic assembly, the kit comprising:
   a laminated wear plate comprising a plurality of ferromagnetic layers; and wherein the laminated wear plate is coated with an electrically conductive material and coupled to the electromagnetic assembly via an adhesive.

19. The kit of claim 18, wherein the electrically conductive material is coated on an outer surface of the laminated wear plate.

20. The kit of claim 18, wherein the electrically conductive material is copper.

* * * * *